United States Patent
Cutler et al.

(10) Patent No.: US 10,391,191 B2
(45) Date of Patent: Aug. 27, 2019

(54) SCENT DIFFUSER

(71) Applicant: Energizer Brands II, LLC, St. Louis, MO (US)

(72) Inventors: Jim Cutler, St. Louis, MO (US); Troy Christiansen, St. Louis, MO (US); Chris Bourne, St. Louis, MO (US)

(73) Assignee: Energizer Brands II, LLC, St. Louis, MO (US)

( * ) Notice: Subject to any disclaimer, the term of this patent is extended or adjusted under 35 U.S.C. 154(b) by 39 days.

(21) Appl. No.: 15/583,613

(22) Filed: May 1, 2017

(65) Prior Publication Data

US 2018/0311394 A1   Nov. 1, 2018

(51) Int. Cl.
  *A61L 9/12*   (2006.01)
(52) U.S. Cl.
  CPC ............ *A61L 9/12* (2013.01); *A61L 2209/134* (2013.01); *A61L 2209/15* (2013.01); *A61L 2209/16* (2013.01)
(58) Field of Classification Search
  CPC ...... A61L 9/12; A61L 9/125; A61L 2209/134; A61L 2209/15; A01M 1/2044; A01M 1/2055; B60H 3/007–0035; B60H 2003/0042–0064
  USPC .................. 239/47, 49, 50, 53–59; 261/64.1, 261/DIG. 68, DIG. 88
  See application file for complete search history.

(56) References Cited

U.S. PATENT DOCUMENTS

| | | | | |
|---|---|---|---|---|
| 2,545,160 A | * | 3/1951 | Miller ................. | A01M 17/006 116/DIG. 22 |
| 2,673,120 A | * | 3/1954 | Bink ................... | A01M 1/2055 206/213.1 |
| 3,908,905 A | * | 9/1975 | Von Philipp ........ | A01M 1/2055 239/55 |
| 8,978,998 B1 | * | 3/2015 | Talley ................. | A61L 9/127 239/51.5 |
| 2008/0093474 A1 | * | 4/2008 | Suissa ................. | A61L 9/122 239/34 |
| 2008/0217426 A1 | * | 9/2008 | Brown ................ | A01M 1/2044 239/45 |
| 2016/0166722 A1 | * | 6/2016 | Mudrick ............. | A61L 9/12 239/55 |

* cited by examiner

*Primary Examiner* — Arthur O. Hall
*Assistant Examiner* — Cody J Lieuwen
(74) *Attorney, Agent, or Firm* — Alston & Bird LLP

(57) ABSTRACT

Scent diffusers (e.g., air fresheners) having adjustable scent diffusion rates may comprise scent intensity adjustment configurations for adjusting the intensity of a fragrance material emitted from the scent diffusers. In certain embodiments, the scent intensity adjustment configuration may take the form of slidable planar scent panels saturated with fragrance composition that may be moved into and out of a hollow body portion. When positioned substantially within the hollow body portion, the scent panels emit fragrance composition at a first rate, and when positioned substantially outside of the hollow body portion, the scent panels emit fragrance at a second rate, faster than the first rate. Alternatively, a scent diffuser may have a body portion containing a scent panel, wherein the body portion has a plurality of ventilation openings to control the rate of fragrance composition diffusion by rotating an adjustment panel to selectively block the ventilation openings of the body portion.

10 Claims, 5 Drawing Sheets

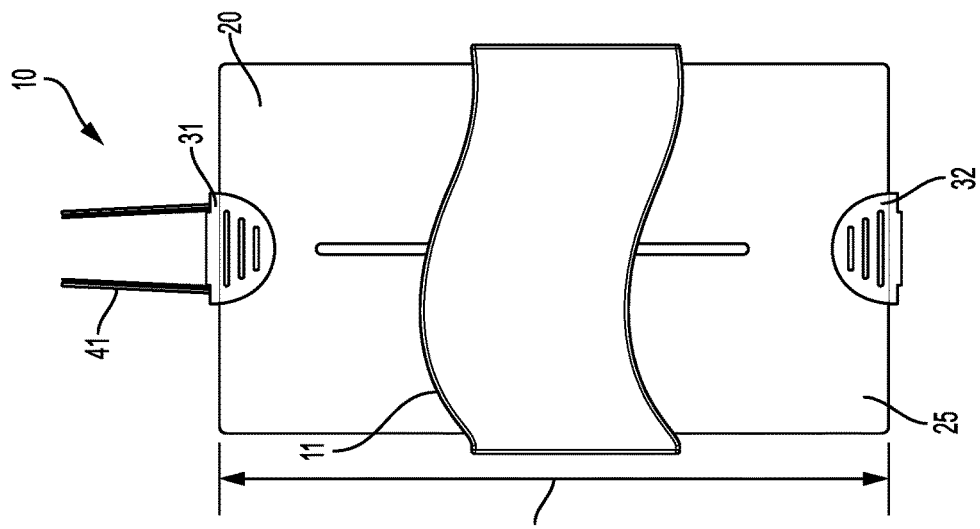
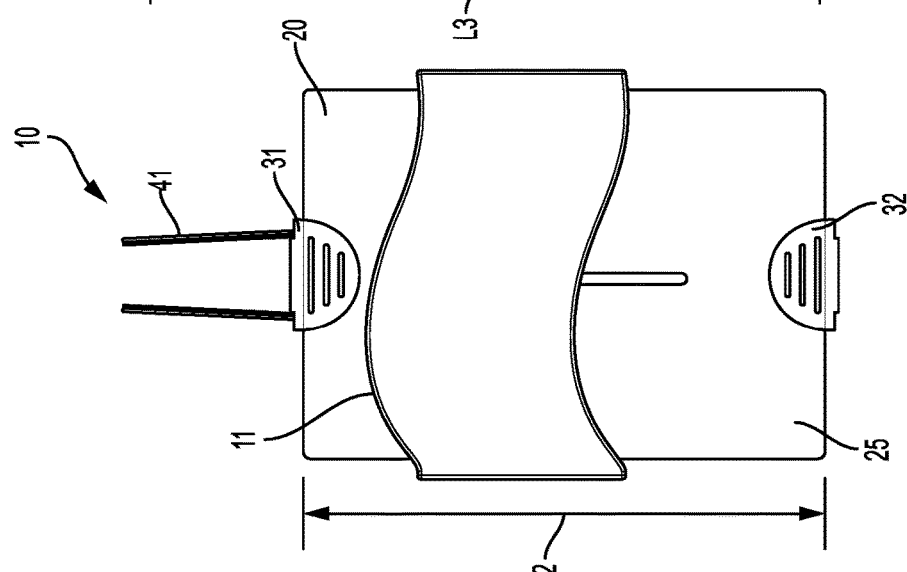
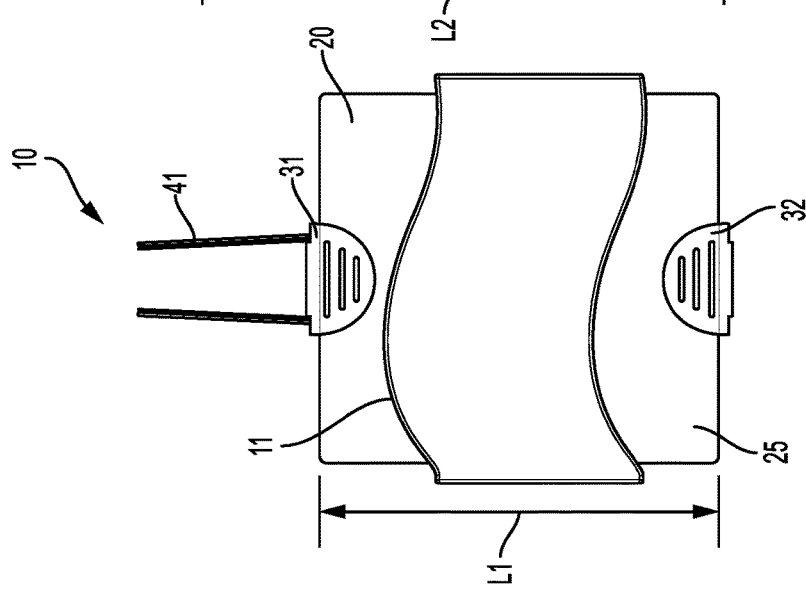

SCENT DIFFUSER

BACKGROUND

Consumer taste for features included in scent diffusers are constantly changing. Accordingly, a need constantly exists for scent diffuser configurations designed to match consumers' continually evolving tastes.

BRIEF SUMMARY

Various embodiments are directed to scent diffusers particularly configured for use as vehicle interior air fresheners. The various configurations enable a user to customize the intensity of a fragrance diffused from the air freshener by adjusting the size of the exposed surface area of one or more fragrance-saturated panels.

Certain embodiments enable a user to adjust the amount of exposed fragrance-saturated panels by sliding one or more fragrance saturated panels relative to a rigid body portion. In a first position, each fragrance panel is positioned substantially within an interior portion of the rigid body portion. The fragrance panels are slidable (e.g., in opposite directions) out of the rigid body portion to a second position in which the fragrance panels are positioned substantially exterior to the rigid body portion.

In other embodiments, a fragrance-saturated disk is positioned within an enclosed body portion. The body portion comprises a plurality of vent openings on at least one side of the body portion, and additionally comprises a rotatable adjustment panel positioned between the body portion and the fragrance-saturated disk having a plurality of apertures that are optionally aligned with the vent openings of the body portion. The rotatable adjustment panel may be rotated between a first position, in which the adjustment panel apertures are aligned with the vent openings of the body portion to provide a maximum amount of exposed surface area of the fragrance-saturated disk within the body portion, and a second position in which the apertures of the body portion are not aligned with the vent openings of the adjustment panel, such that the fragrance-saturated disk is substantially covered by the combination of the adjustment panel and the body portion.

Certain embodiments are directed to a scent diffuser comprising a first scent panel and a second scent panel, each of the first and second scent panels saturated with a fragrance composition. In certain embodiments, the second scent panel is slidable relative to the first scent panel to adjust a rate of fragrance composition diffusion from each of the first scent panel and the second scent panel.

Various embodiments are directed to a scent diffuser comprising a hollow body having one or more sidewalls collectively defining a body interior, wherein the hollow body defines at least one open end and at least one slide pin extending away from an interior surface of at least one sidewall into the body interior; at least one planar scent panel positioned within the body interior and extending through the open end of the body portion, wherein the planar scent panel is at least partially saturated with a fragrance composition and defines a groove slidably engaged with the slide pin. In certain embodiments, the planar scent panel is slidable between: a compressed position in which a first surface area of the planar scent panel is positioned within the body interior and the slide pin is positioned adjacent a first end of the groove; and an expanded position in which a second surface area of the planar scent panel is positioned within the body interior and the slide pin is positioned against a second end of the groove, wherein the first surface area is greater than the second surface area. In certain embodiments, the planar scent panel may be frictionally engaged with the interior of the body portion to maintain a user selected positioning of the scent panel relative to the body portion.

In certain embodiments, the hollow body defines a first open end and a second open end positioned opposite the first open end, and defines two slide pins, wherein the two slide pins comprise a first slide pin extending away from an interior surface of a first sidewall and a second slide pin extending away from an interior surface of a second sidewall. Moreover, the at least one planar scent panel may comprise a first planar scent panel and a second planar scent panel, wherein each of the first planar scent panel and the second planar scent panel is at least partially saturated with the fragrance composition and wherein: the first planar scent panel defines a first groove slidably engaged with the first slide pin, and wherein the first planar scent panel is slidable through the first open end of the hollow body between a compressed position and an expanded position; and the second planar scent panel defines a second groove slidably engaged with the second slide pin, and wherein the second planar scent panel is slidable through the second open end of the hollow body between a compressed position and an expanded position. In certain embodiments, the first planar scent panel is slidable independently of the second planar scent panel.

Various embodiments are directed to a scent diffuser comprising: a hollow body surrounding a body interior, the hollow body defining a first end and a second end, wherein the second end is parallel with the first end and is separated from the first end by one or more sidewalls extending between the first end and the second end, and wherein the first end and the second end each define a plurality of ventilation openings extending through the hollow body; a fragrance panel saturated at least in part with a fragrance composition, wherein the fragrance panel is positioned within the hollow body; at least one adjustment panel positioned within the body interior and rotatably secured relative to an interior surface of the first end, wherein the adjustment panel defines a plurality of apertures extending therethrough that may be selectably aligned with the ventilation openings extending through the first end of the hollow body. In various embodiments, the adjustment panel is rotatable between: an open configuration in which the plurality of apertures of the adjustment panel are aligned with the ventilation openings of the hollow body; and a closed configuration in which the plurality of apertures of the adjustment panel are not aligned with the ventilation openings of the body, and the ventilation openings of the body portion are blocked by a portion of the adjustment panel.

In certain embodiments, the at least one adjustment panel is a first adjustment panel, and the scent diffuser further comprises a second adjustment panel positioned within the body interior and rotatably secured relative to an interior surface of the second end, wherein the second adjustment panel defines a plurality of apertures extending therethrough that may be selectably aligned with the ventilation openings extending through the second end of the hollow body, the second adjustment panel is rotatable between: an open configuration in which the plurality of apertures of the second adjustment panel are aligned with the ventilation openings of the hollow body; and a closed configuration in which the plurality of apertures of the second adjustment panel are not aligned with the ventilation openings of the body, and the ventilation openings of the body portion are blocked by a portion of the adjustment panel. Moreover, the first adjustment panel may be movable independently of the second adjustment panel.

BRIEF DESCRIPTION OF THE SEVERAL VIEWS OF THE DRAWINGS

Reference will now be made to the accompanying drawings, which are not necessarily drawn to scale, and wherein:

FIGS. 3-5 show the scent diffuser of FIG. 1 in various activation levels;

DETAILED DESCRIPTION

Figure 1:
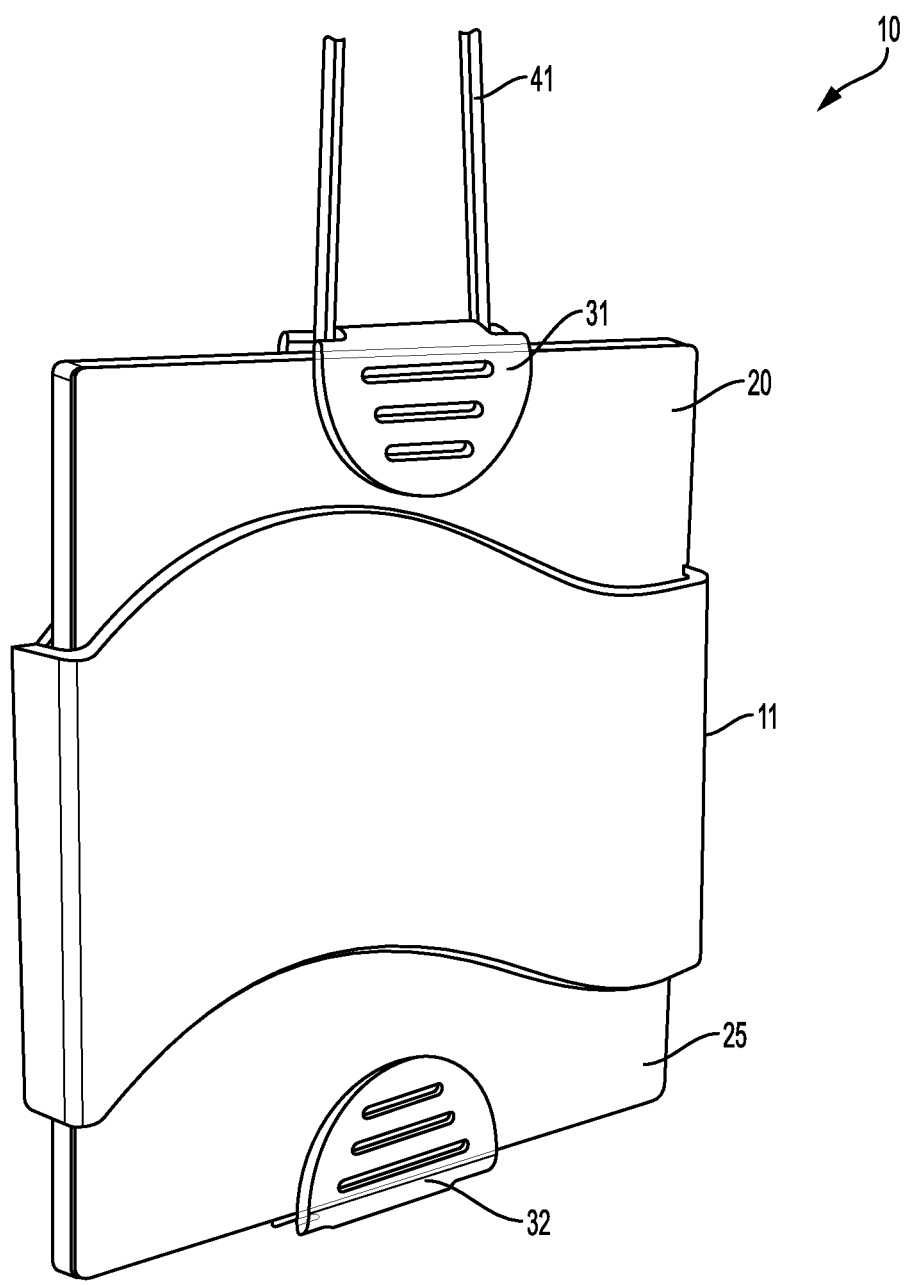
FIG. 1 shows a scent diffuser according to one embodiment.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Various embodiments are directed to scent diffusers configured for diffusing a fragrance (e.g., a scented oil) from a substrate (e.g., a paper panel) into environmental air. Specifically, various embodiments are directed to scent diffusers specifically configured for use in an automobile interior.

Certain embodiments comprise one or more slidable panels saturated with a fragrance that are configured to slide into and out of a body portion. The body portion may comprise a hollow shell having opposite open ends through which the one or more panels may slide. The panels may slide between a first, compressed position in which a substantial portion of the panel is positioned within the interior of the body portion and a small portion adjacent a first end is positioned outside of the body portion, and a second, expanded position in which a substantial portion of the panel is positioned outside of the body portion and a small portion adjacent a second end is positioned within the body portion. Accordingly, in the first position a substantial portion of the panel remains protected from the environmental air surrounding the scent diffuser, thereby slowing the rate of diffusion of the fragrance from the panel into the environmental air. In the second position, a substantial portion of the panel is exposed to the environmental air surrounding the scent diffuser, thereby increasing the rate of diffusion of the fragrance from the panel into the environmental air. Accordingly, by adjusting the amount of the panel that is positioned within the body portion, a user can control the intensity of fragrance emitted by the scent diffuser.

Other embodiments comprise a panel saturated with a fragrance that is positioned within an enclosed body portion of a scent diffuser. The body portion comprises an adjustable vent mechanism to adjust the amount of air that may flow into the body portion, thereby adjusting the intensity of fragrance emitted by the scent diffuser. Specifically, the body portion comprises a plurality of vent openings extending therethrough, and comprises an adjustment panel rotatably secured relative to the body portion, and positioned between the body portion and the fragrance-saturated panel. The adjustment panel additionally comprises a plurality of apertures extending therethrough. The apertures of the adjustment panel may be selectably aligned with the vent openings of the body portion to adjust the amount of air permitted to enter the body portion, and by extension, the amount of air permitted to flow around the fragrance-saturated panel.

Slidable Scent Diffuser

FIGS. 1-5 illustrate various configurations of a scent diffuser 10 according to one embodiment. As shown in FIG. 1, the scent diffuser 10 comprises a body portion 11, a first scent panel 20, and a second scent panel 25. In the illustrated embodiment of FIG. 1, the first scent panel 20 and the second scent panel 25 may have corresponding handle portions 31, 32 secured thereto, the handle portions 31, 32 enabling a user to slide the corresponding scent panels 20, 25 without contacting the fragrance saturated portions of the scent panels 20, 25. Moreover, as illustrated in FIG. 1, the scent diffuser 10 may comprise a support component configured to support the scent diffuser 10 in a desired position, such as the lanyard 41 shown in FIG. 1.

Figure 2:
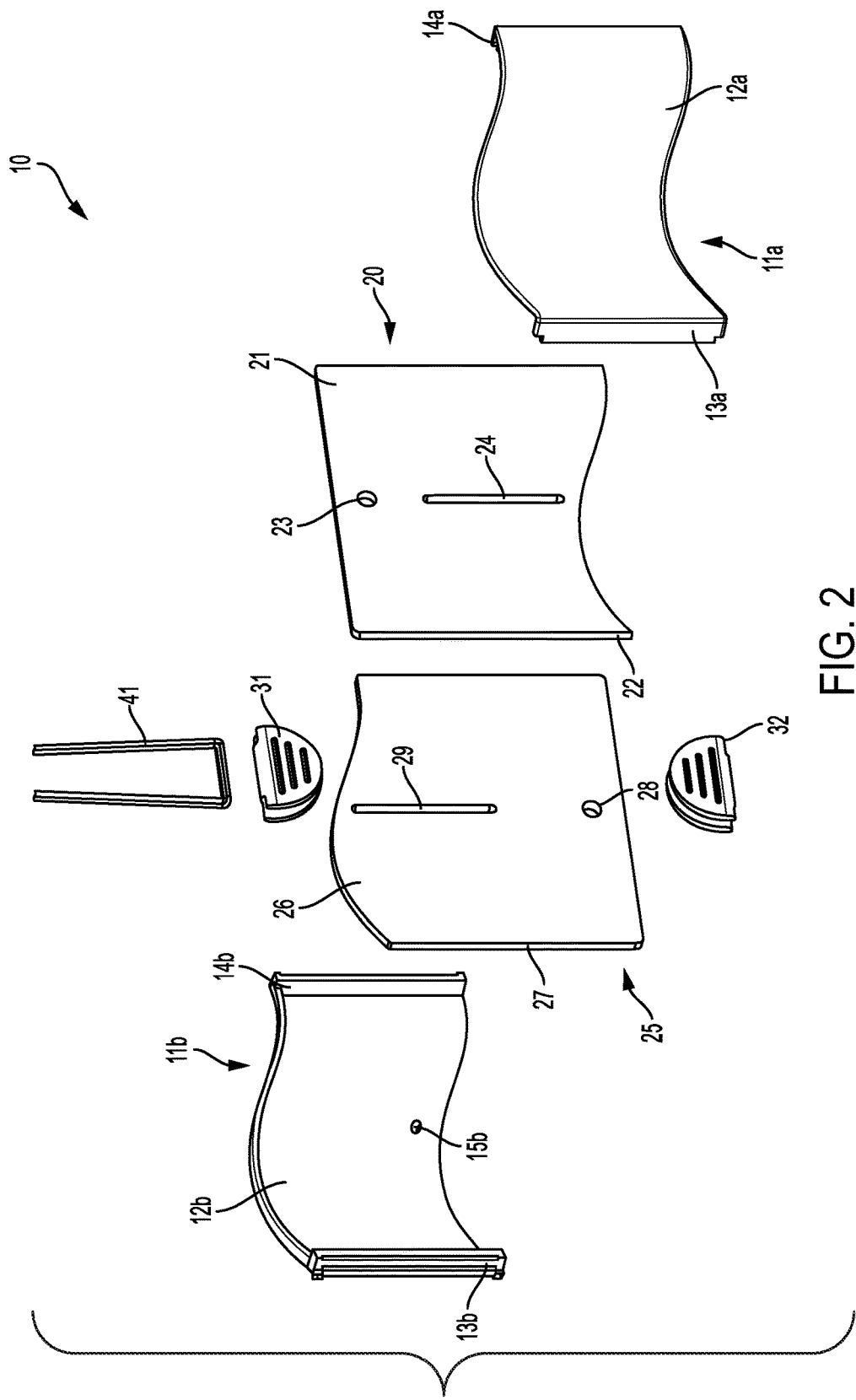
FIG. 2 shows an exploded view of the scent diffuser of FIG. 1.

In various embodiments, the body portion 11 comprises a rigid material, such as plastic (e.g., polyvinyl chloride and/or another polymer), metal (e.g., aluminum), and/or the like. In certain embodiments, the rigid material is substantially non-porous, such that a fragrance material saturating one or more of the scent panels 20, 25 does not migrate into the body portion 11. As shown in FIGS. 1 and 2, the latter of which illustrating an exploded view of the scent diffuser 10, the body portion 11 defines a hollow member having at least one open end. For example, in the illustrated embodiment of FIGS. 1-2, the body portion 11 defines a first open end and a second open end, wherein the first and second open ends are opposite one another. Accordingly, in the illustrated embodiment of FIG. 1, the body portion 11 defines a hollow tube having open ends through which the scent panels 20, 25 may travel.

Moreover, as shown in FIG. 1, the body portion 11 is at least substantially rectangular, having opposite and parallel elongated sides and opposite and parallel short sides, wherein the short sides are at least substantially perpendicular to the elongated sides. Collectively, the plurality of elongated sides and the plurality of short sides define an interior portion of the body portion 11 between the plurality of sides. The interior portion having an at least substantially perpendicular cross section (i.e., parallel to the open ends of the body portion 11). As shown in the figures, the open ends of the body portion 11 may define non-linear portions, for example, to provide a desired aesthetic effect.

The body portion 11 may comprise one or more body components collectively forming the body portion 11. For example, in the illustrated embodiment of FIG. 2, the body portion 11 comprises two body components 11a, 11b that may be secured relative to one another to collective form the body portion 11. As shown in FIG. 2, the body portion comprises a first body component 11a and a second body component 11b having features mirroring those of the first body component 11a.

As shown in FIG. 2, each body component 11a, 11b defines an elongated planar sidewall 12a, 12b forming the front wall and rear wall of the body portion 11, respectively. Specifically, in the illustrated embodiment of FIG. 2, the first body component 11a comprises a first elongated planar sidewall 12a, and the second body component 11b comprises a second elongated planar sidewall 12b. When assembled (as shown in FIG. 1), the first elongated planar sidewall 12a is at least substantially parallel with the second elongated planar sidewall 12b.

With reference again to FIG. 2, each body component 11a, 11b defines a first connecting sidewall 13a, 13b, and a second connecting sidewall 14a, 14b. The first connecting sidewalls 13a, 13b of a respective body component are positioned opposite and at least substantially parallel to the second connecting sidewalls 14a, 14b of the same body component. As shown in FIG. 2, the connecting sidewalls 13a, 13b, 14a, 14b extend at least substantially perpendicularly away from side edges of the elongated planar sidewalls 12a, 12b. Accordingly, each body component 11a, 11b may define an at least substantially "U"-shaped cross-section.

The first connecting sidewalls 13a, 13b of the body components 11a, 11b comprising mating connecting features, to enable the body components 11a, 11b to be secured relative to one another (as shown in FIG. 1). For example, the first connecting sidewall 13a of the first body component 11a may be configured to snap onto the first connecting sidewall 13b of the second body component 11b. In the illustrated embodiments of FIGS. 1 and 2, the first connecting sidewall 13a of the first body component 11a may be configured to connect with the first connecting sidewall 13b of the second body component 11b such that the first connecting sidewall 13a of the first body component 11a defines a portion of the exterior surface of the body portion 11 and the first connecting sidewall 13b of the second body component 11b defines a portion of the interior surface of the body portion 11. Moreover, in the illustrated embodiment of FIGS. 1-2, the first connecting sidewalls 13a, 13b are fixedly secured relative to one another when connected, such that the first connecting sidewall 13a cannot move relative to the first connecting sidewall 13b (e.g., in a direction parallel or perpendicular to the direction of travel of the slidable scent panels 20, 25, as discussed in greater detail herein).

The second connecting sidewalls 14a, 14b have a configuration analogous to the first connecting sidewalls 13a, 13b. Accordingly the second connecting sidewalls 14a, 14b comprise mating connecting features to enable the body components 11a, 11b to be secured relative to one another (as shown in FIG. 1). Like the first connecting sidewalls 13a, 13b, the second connecting sidewalls 14a, 14b are fixedly secured relative to one another when connected, such that the second connecting sidewall 14a cannot move relative to the second connecting sidewall 14b (e.g., in a direction parallel or perpendicular to the direction of travel of the slidable scent panels 20, 25, as discussed in greater detail herein).

Although illustrated such that the first body component 11a is securable relative to the second body component 11b via mating connecting features of the connecting sidewalls 13a, 13b, 14a, 14b, it should be understood that the first body component 11a may be securable relative to the second body component 11b via any of a variety of fastening mechanisms. For example, the body components 11a, 11b may be securable relative to one another via one or more fasteners (e.g., screws, bolts, threaded fasteners, nails, pins, adhesives, and/or the like).

With reference again to FIG. 2, one or more of the body components 11a, 11b may comprise a slide pin configured to interact with corresponding slide slots within the slidable scent panels (as discussed in greater detail herein). For example, second body component 11b has a corresponding slide pin 15b extending at least substantially perpendicularly away from the interior surface of the elongated sidewall 12b toward the interior of the body portion 11, as shown in the illustrated embodiment of FIG. 2. Although not shown, first body component 11a may additionally have a corresponding slide pin extending toward the interior of the body portion 11. In various embodiments, the slide pin on the first body component 11a may be configured to engage a first scent panel 20, and the slide pin 15b on the second body component 11b may be configured to engage a second scent panel 25.

In the illustrated embodiment of FIG. 2, the slide pin 15b is located proximate the lower edge of the body component 11b (located between a centerline of the body component 11b and a bottom edge of the body component 11b). As discussed in greater detail herein, the second scent panel 25 is configured to extend beyond the lower edge of the body component 11b, and accordingly the positioning of the slide pin 15b relative to the lower edge of the body component 11b minimizes the amount of scent panel 25 that remains within the body portion 11 while the scent panel 25 is in an extended configuration.

The slide pin of the first body component 11a may be similarly positioned proximate the top edge of the body component 11a. Because the first scent panel 20 is configured to extend beyond the top edge of the body component 11a, the positioning of the slide pin relative to the top edge of the body component 11a minimizes the amount of scent panel 20 that remains within the body portion 11 while the scent panel 20 is in an extended configuration.

In the illustrated embodiment of FIGS. 1 and 2, the scent diffuser 10 comprises a first scent panel 20 and a second scent panel 25. In certain embodiments, the scent panels may each comprise a porous, rigid material, such as laminated paper, cardboard, cellulose and/or the like. The scent panels may be saturated at least in part with a fragrance material (e.g., a fragrance oil) that may evaporate or otherwise diffuse into air surrounding the scent diffuser 10.

As shown in FIG. 2, each scent panel 20, 25 may define opposing and parallel large planar surfaces 21, 26. Specifically, scent panel 20 defines opposing and parallel large planar surfaces 21 separated by a side edge 22 surrounding the large planar surfaces 21. Similarly, scent panel 25 defines opposing and parallel large planar surfaces 26 separated by a side edge 27 surrounding the large planar surfaces 26. In the illustrated embodiment of FIG. 2, the side edges 22, 27 of scent panels 20, 25 each comprise at least two parallel and opposite edge portions extending in a direction at least substantially parallel with the sliding direction of the scent panels 20, 25. The parallel and opposite edge portions are configured to slide relative to the body portion 11 as the scent panels 20, 25 are slid relative to the body portion 11.

Moreover, in the illustrated embodiment of FIGS. 1 and 2, the large planar surfaces 21, 26 have a width (measured perpendicular to and between the parallel and opposite edge portions) substantially equal to a width of the interior of the body portion 11. Accordingly, the parallel and opposite edge portions of the side edges 22, 27 are configured to frictionally engage the interior walls of the body portion 11 to maintain a desired positioning of the scent panel 20, 25 relative to the body portion 11.

As shown in FIG. 2, the scent panels 20, 25 each define a handle engagement feature 23, 28 (e.g., a hole). The handle engagement feature 23, 28 is configured to enable a handle to be secured relative to the scent panels 20, 25. For example, in the illustrated embodiment of FIGS. 1 and 2, the handle 31, 32 defines an at least substantially "C"-shaped panel configured to fit around an edge of scent panel 20, 25 and extend at least partially along the length of the scent panel 20, 25. For example, the handle 31, 32 extends at least beyond the handle engagement feature 23, 28 such that a portion of the handle 31, 32 engages the handle engagement feature to secure the handle 31, 32 relative to the scent panel. As just one non-limiting example, the handle 31, 32 may define one or more engagement pins configured to fit within a handle engagement hole of the scent panel, such that the handle 31, 32 is prevented from sliding relative to the scent panel 20, 25. As shown in FIG. 1, the handle 31, 32 fits around an edge of a respective scent panel 20, 25 to provide a non-saturated surface for a user to pull and/or push the scent panel 20, 25 relative to a body portion 11.

In various embodiments, the handle 31, 32 comprises a rigid material (e.g., plastic) formed in a "C" shape and having an interior portion sized to fit around an edge of a scent panel 20, 25. However, in certain embodiments, the handle 31, 32 comprises a flexible material (e.g., a flexible plastic material) that may be flexed around an edge of the scent panel 20, 25. As a specific example, the handle 31, 32 may comprise an at least substantially planar flexible material that may be flexed around an edge of the scent panel 20, 25.

Moreover, as shown in the illustrated embodiment of FIGS. 1 and 2, at least one handle 31, 32 may be configured to secure a scent diffuser support feature (e.g., lanyard 41) relative to the scent diffuser 41. For example, the lanyard 41 shown in FIGS. 1 and 2 may be configured to suspend the scent diffuser 10 from a rearview mirror of an automobile.

The scent panels 20, 25 may additionally define a slide groove 24, 29 extending through the scent panels 20, 25 between the large planar sides 21, 26. As discussed herein, the slide grooves 24, 29 are configured to engage corresponding slide pins of the body components 11a, 11b to limit the slide distance of the scent panels 20, 25 relative to the body portion 11. Accordingly, the slide grooves 24, 29 enable the slide panels 20, 25 to slide between a first (e.g., compressed) position in which the slide panel is positioned within the body portion 11 and a second (e.g., expanded) position in which the slide panel is positioned at least substantially outside of the body portion 11. When a scent panel is in the first position, the slide pin is positioned against a first end of a corresponding slide groove, and when the scent panel is in the second position, the slide pin is positioned against an opposite second end of the corresponding slide groove.

FIGS. 3-5 illustrate the scent diffuser 10 in various configurations in which each of the scent panels 20, 25 are in a first position or a second position. As shown in FIGS. 3-5, the scent panels 20, 25 may be independently movable relative to the body portion 11. For example, a first scent panel 20 may be movable relative to the body portion 11 while the second scent panel 25 remains stationary relative to the body portion 11. For example, FIG. 3 illustrates a scent diffuser 10 in which both the first scent panel 20 and second scent panel 25 are in a first, compressed position positioned at least substantially within the body portion 11. As shown in FIG. 3, the first scent panel 20 and the second scent panel 25 at least substantially overlap one another when in the first, compressed position. Accordingly, the amount of exposed surface area of each of the first scent panel 20 and the second scent panel 25 is limited by the amount of surface area of the first scent panel 20 and the second scent panel 25 that is positioned within the body portion 11, and by the amount of surface area of the first scent panel 20 that overlaps a portion of the second scent panel 25. In the first, compressed configuration, the scent diffuser 10 has a first overall length L1. FIG. 4 illustrates a scent diffuser 10 in which the first scent panel 20 is in a first position and the second scent panel 25 is in a second position. In such a configuration, the scent diffuser 10 has a second overall length L2 that is longer than the first overall length L1. Moreover, when in the configuration shown in FIG. 4, the rate of diffusion of fragrance composition from the first scent panel 20 is less than the rate of fragrance composition from the second scent panel 25, because the first scent panel 20 is positioned at least substantially within the body portion 11 while the second scent panel is positioned at least substantially outside of the body portion 11. Finally, FIG. 5 illustrates the scent diffuser 10 in which both the first scent panel 20 and the second scent panel 25 are in a second configuration. In such a configuration, the scent diffuser 10 has a third overall length L3 that is greater than the second overall length L2. In the configuration of FIG. 5, the first scent panel 20 does not overlap the second scent panel 25, and both of the first scent panel 20 and the second scent panel 25 are positioned at least substantially outside of the body portion 11. Accordingly, the rate of scent diffusion of the first scent panel 20 is at least substantially the same as the rate of scent diffusion of the second scent panel 25.

Accordingly, in the configuration shown in FIG. 3, the scent diffuser 10 is configured to diffuse scent at a minimal diffusion rate and in the configuration shown in FIG. 5, the scent diffuser 10 is configured to diffuse scent at a maximum diffusion rate. When in the configuration shown in FIG. 4, the scent diffuser 10 is configured to diffuse scent at a medial rate. As noted herein, each of the scent panels may be independently and infinitely adjustable between the first configuration and the second configuration, and accordingly the rate of scent diffusion may be infinitely adjustable between the minimal rate of diffusion and the maximum rate of diffusion. As noted herein, the linear portions of the side edges 22, 27 of the scent panels frictionally engage the interior walls of the body portion 11, such that scent panels are configured to maintain a desired configuration relative to the body portion 11. In various embodiments, the position of the scent panels 20, 25 may be adjusted relative to the body portion 11 by applying a tensile force (e.g., a pulling force) to the scent panel (e.g., at the handle 31, 32) and/or by applying a compressive force (e.g., a pushing force) to the scent panel (e.g., at the handle 31, 32) to move the scent panel relative to the body portion 11. Specifically, the tensile force and/or the compressive force may be applied along a major axis of the scent panel, parallel to the direction of travel of the scent panel relative to the body portion 11. For example, to move the scent panel to the first position, a compressive force may be applied to the scent panel in a direction parallel to the direction of travel of the scent panel to move the scent panel into the interior of the body portion 11. Similarly, to move the scent panel to the second position, a tensile force may be applied to the scent panel in a direction parallel to the direction of travel of the scent panel to move the scent panel out of the body portion 11. Moreover, as mentioned, each scent panel 20, 25 may be moved independently, thereby providing additional control to the user over the level of scent diffusion from the scent diffuser 10.

Rotatable Scent Diffuser

Figure 6:
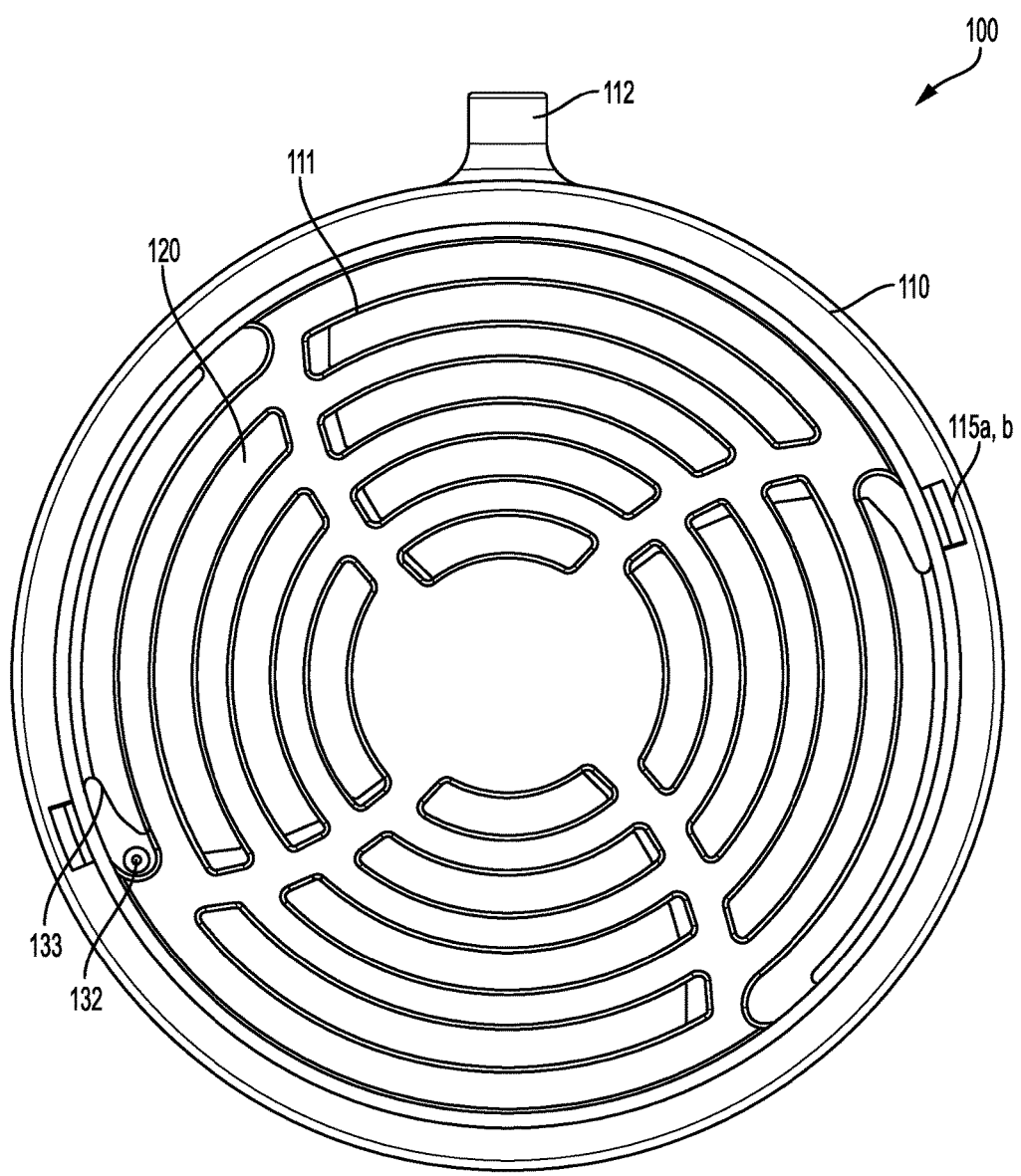
FIG. 6 shows a scent diffuser according to another embodiment.
Figure 7:
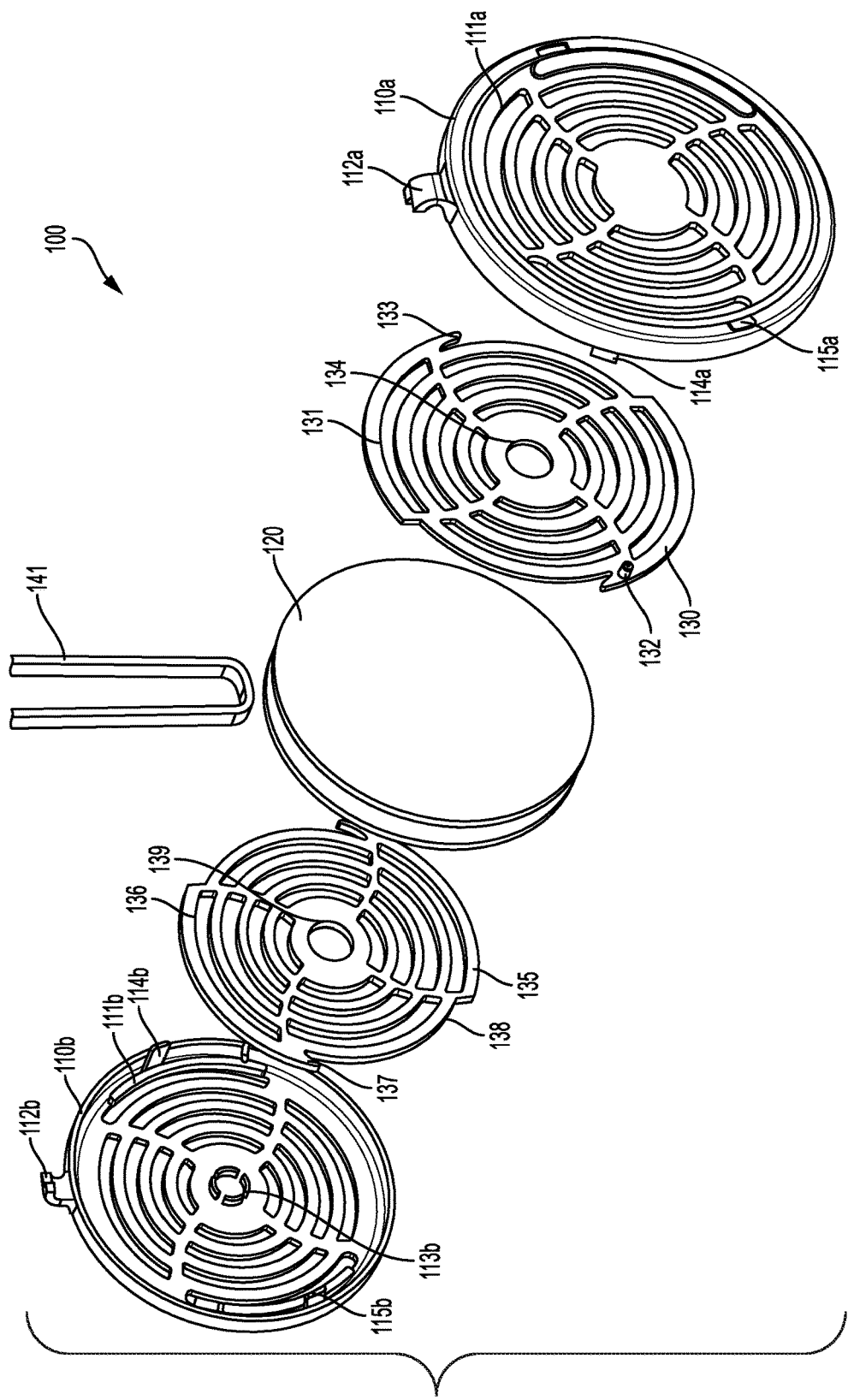
FIG. 7 shows an exploded view of the scent diffuser of FIG. 6.

With reference now to FIGS. 6 and 7 a scent diffuser 100 according to a second embodiment is shown. Like the scent diffuser 10 described in reference to FIGS. 1-5, the scent diffuser 100 provides an adjustment mechanism for adjusting the rate of scent diffusion into an environment surrounding the scent diffuser 100 (e.g., the interior of an automobile). Specifically, scent diffuser 100 comprises an adjustment mechanism that enables a user to adjust the amount of exposed surface area of a fragrance-saturated panel 120 within the scent diffuser 100, thereby adjusting the rate of diffusion of the fragrance (e.g., a fragrance oil) into air passing into and/or through the scent diffuser 100.

FIG. 6 is a front view of a scent diffuser 100 according to one embodiment. As shown in FIG. 6, the scent diffuser comprises a body portion 110 housing the various components of the scent diffuser 100. Although shown as being generally round (e.g., at least substantially cylindrical, considering an at least substantially linear depth, as evidence by FIG. 7), it should be understood that the body portion 110 may be any of a variety of shapes, including, for example, rectangular, triangular, ovular, and/or the like. As will be described in greater detail herein, one or more adjustment panels 130, 131 should be configured to rotate within the body portion 110 without intersecting walls of the body portion, however the overall shape of the body portion 110 is not limited by the functionality of the adjustment panels 130, 131.

With reference again to FIG. 6, the body portion 110 comprises a plurality of ventilation openings, such as vent slots 111 shown in FIG. 6. The ventilation openings are configured to provide an air travel path into and out of the air diffuser 100 to enable air to pass around and/or through the fragrance-saturated panel 120 positioned within scent diffuser 100. As shown in FIG. 6, the ventilation openings are positioned and aligned along concentric circles centered about a mid-point of the body portion 110. For example, in the illustrated embodiment of FIG. 6, each vent slot 111 defines a segment of a circle concentric with a mid-point of the body portion 110. Moreover, as shown in FIG. 6, ventilation openings aligned with a common concentric circle may be spaced such that the width of each ventilation opening (the width being measured along the concentric circle) is less than or equal to the width of the space between ventilation openings aligned with the common concentric circle (each space being a solid portion of the body portion 110). With reference to FIG. 6, two vent slots 111 are aligned with each of a variety of concentric circles, and the pairs of aligned vent slots are spaced at least approximately 180 degrees relative to one another. Each vent slot 111 has a width less than or equal to 90 degrees (measured from the mid-point of the body portion), and according the space between aligned vent slots has a length equal to or greater than 90 degrees.

Moreover, as shown in FIG. 6, a plurality of vent slots 111 may be aligned along a single radius extending away from the mid-point of the body portion 110. Each of the vent slots 111 may have an at least substantially equal height (measured along a radius extending away from the mid-point of the body portion 110). Moreover, vent slots 111 aligned along a common radius may be spaced by a distance equal to or less than the height of each vent slot 111. As will be described in greater detail herein, an adjustment panel 130, 135 has a corresponding configuration of ventilation apertures and spaces therebetween, such that the adjustment panel 130, 135 may be rotated relative to the body portion 110, to selectively align the ventilation apertures of the adjustment panel 130, 135 with the ventilation openings of the body portion 110 (e.g., to enable a maximum air flow into the interior of the body portion 110), and to selectively align solid spaces of the adjustment panel 130, 135 with the ventilation openings of the body portion 110 to thereby block the ventilation openings of the body portion 110 (e.g., to provide a minimum air flow into the interior of the body portion 110).

FIG. 7 illustrates an exploded view of the scent diffuser 100 of FIG. 6. As shown in FIG. 7, the body portion 110 comprises a first body component 110a and a second body component 110b that may be coupled to one another to provide the body portion 110. For example, the first body component 110a and second body component 110b may be corresponding coupling features 115a, 115b (e.g., a male tab and female slot) configured for coupling the first body component 110a to the second body component 110b. For example, a coupling tab 115b may be configured to fit within and engage a corresponding coupling slot 115a to selectively couple the first body component 110a to the second body component 110b.

Moreover, as shown in FIG. 7, each of the first body component 110a and second body component 110b may define a solid body wall (e.g., comprising a rigid material, such as plastic, metal, wood, and/or the like) surrounding a hollow interior portion. When configured such that the first body component 110a is secured relative to the second body component 110b, the body portion 110 thereby defines a hollow shell, within which additional components of the scent diffuser 100 are positioned.

The first body component 110a and second body component 110b may be similarly configured, as shown in FIG. 7. For example, each of the first body component 110a and second body component 110b may define a plurality of ventilation openings extending through face surfaces of the body components 110a, 110b, wherein the face surfaces are on generally parallel and opposite sides of the body portion 110. In certain embodiments, such as that shown in FIG. 7, the ventilation openings are configured as vent slots 111a, 111b as discussed herein.

Moreover, as shown in FIGS. 6 and 7, the body components 110a, 110b each comprise support components, such as hanger portions 112a, 112b as shown in FIG. 7. Collectively, the hanger portions 112a, 112b define a hanger 112 from which the scent diffuser 100 may be suspended (e.g., via lanyard 141).

Each of the body components 110a, 110b may be configured to engage a corresponding adjustment panel 130, 135 that is rotatably secured relative to the body component 110a, 110b. As shown in FIG. 7, the body components 110a, 110b defines an alignment feature 113b (alignment feature of body component 110a not visible in the orientation of FIG. 7) configured to engage a corresponding alignment aperture 134, 139 of the adjustment panel 130, 135. As shown in FIG. 7, the alignment feature 113b may define one or more protrusions extending away from the face surface of the body component 110a, 110b toward the interior of the body portion 110, and the one or more protrusions collectively define a circular alignment feature 113b about which the adjustment panel 130, 135 may rotate (e.g., about alignment aperture 134, 139 positioned around the alignment feature 113b). In certain embodiments, alignment features 113b may be configured to lockably engage the alignment aperture 134, 139 of a corresponding adjustment panel 130, 135 to prevent the alignment aperture 134, 139 from disengaging the alignment feature 113b.

As noted above, each adjustment panel 130, 135 defines a plurality of ventilation apertures 131, 136 corresponding to the plurality of ventilation openings 111a, 111b of the body components 110a, 110b. Accordingly, the ventilation apertures 131, 136 of each adjustment panel 130, 135 may be selectably aligned with the ventilation openings 111a, 111b of the body components 131, 136 to define a linear air flow path through the aligned ventilation openings and ventilation apertures 111a, 111b, 131, 136 into the fragrance-saturated panel 120 positioned centrally within the body portion 110 (the fragrance-saturated panel 120 being an at least substantially circular disk having a configuration similar to fragrance-saturated scent panels 20, 25, discussed above).

As shown in FIGS. 6 and 7, the adjustment panels 130, 135 each have at least one control feature 132, 137 configured to extend through a ventilation slot 111 of the body portion 110 and beyond an external face surface of the body portion 110. For example, the control features 132, 137 may each comprise a pin extending away from a surface of the adjustment panel 130, 135 and through a vent slot 111 of the body portion 110 such that a user can move the control feature 132, 137 relative to the body portion 110 to thereby rotate the adjustment panel 130, 135 relative to the body portion 110.

In the illustrated embodiment of FIG. 6, the control feature 132, 127 is movable relative to the body portion 110 between a first position at least substantially adjacent a first end of a corresponding vent slot 111 and a second position at least substantially adjacent a second end of the corresponding vent slot 111 opposite the first end. When the control feature 132, 137 is in the first position, the adjustment panel 130, 135 is rotated such that the ventilation apertures of the adjustment panel 130, 135 are aligned with the ventilation openings of the body portion 110 to enable unimpeded air flow through the scent diffuser 100 to the fragrance saturated disk 120 within the center of the body portion 110. When the control feature 132, 137 is in the second position, the adjustment panel 130, 135 is rotated such that the ventilation openings of the body portion are blocked by solid spaces of the adjustment panel 130, 135 (e.g., between ventilation apertures) to substantially block air flow through the scent diffuser 100 to the fragrance-saturated panel. Accordingly, by adjusting the control feature 132, 137 between the first position and the second position, a user can change the amount of air flow through the scent diffuser 100 to the fragrance-saturated panel 120 positioned therein. In certain embodiments, the amount of air flow enabled through the body portion 110 (and accordingly the intensity of fragrance emitted by the scent diffuser 100) is infinitely adjustable based on the position of the control feature 132, 137 relative to the first position and the second position. For example, positioning the control feature 132, 137 substantially equally spaced between the first position and the second position corresponds to an adjustment panel 130, 135 rotational position in which approximately half of each ventilation opening of the body portion 110 is blocked and approximately half of each ventilation opening of the body portion 110 is aligned with a corresponding ventilation aperture 131, 136 of the adjustment panel 130, 135. Moreover, the interface between the alignment feature 113b and the corresponding alignment apertures 134, 139 may define a frictional engagement therebetween, such that the frictional forces generated between the alignment feature 113b and corresponding alignment apertures 134, 139 may be sufficient to maintain the relative rotational position of the adjustment panel 130, 135 relative to the body portion 110.

As shown in FIG. 7, each adjustment panel 130, 135 may additionally define a stop travel path 133, 138 extending at least partially around the perimeter of the corresponding adjustment panel 130, 135. Each stop travel path 133, 138 may be defined as an open-sided slot defined within the perimeter of the corresponding adjustment panel 130, 135. In certain embodiments, the length of each stop travel path 133, 138 (measured along the circumference of the adjustment panel 130, 135) may correspond to the circumferential distance between the first position and the second position of the control features 132, 137. In certain embodiments, the stop travel path 133, 138 may be positioned relative to a corresponding body component 110a, 110b such that a stop pin 114a, 114b extending away from a body component 110a, 110b toward an interior of the body portion 110 is positioned within the stop travel path 133, 138. The combination of the stop pins 114a, 114b and the stop travel paths 133, 138 provide additional limits to the rotational travel distance of the adjustment panel 130, 135 relative to the body portion 110. Specifically, when the control feature 132, 137 is in the first position, the stop travel path 133, 138 is positioned such that a first end of the stop travel path 133, 138 is positioned adjacent a first side of the stop pin 114a, 114b; and when the control feature 132, 137 is in the second position, the stop travel path 133, 138 is positioned such that a second end of the stop travel path 133, 138 is positioned adjacent a second side of the stop pin 114a, 114b. Accordingly, the adjustment panel 130, 135 may be rotated relative to the body portion 110 between a first position and a second position. In the first position, the ventilation apertures of the adjustment panel 130, 135 are aligned with the ventilation apertures of the body portion 110 to enable unimpeded air flow into the interior of the scent diffuser 100; the control feature 132, 137 is positioned adjacent a first end of a ventilation slot; and the first end of the stop travel path 133, 138 is positioned adjacent a first side of a stop pin 114a, 114b. In the second position, the solid spaces of the adjustment panel 130, 135 are aligned with the ventilation openings of the body portion 110 to impede air flow into the interior of the scent diffuser 100; the control feature 132, 137 is positioned adjacent a second end of a ventilation slot; and the second end of the stop travel path 133, 138 is positioned adjacent a second side of a stop pin 114a, 114b.

In certain embodiments, the rotational position of the first adjustment panel 130 may be changed independently of the rotational position of the second adjustment panel 135, to provide additional customization to the amount of air permitted to flow into the interior of the scent diffuser 110, and accordingly to the rate of fragrance diffusion from the fragrance-saturated panel 120 position centrally within the body portion 110 (e.g., positioned between the first adjustment panel 130 and the second adjustment panel 135).

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

As just one example modification, scent diffuser 10 may comprise only one scent panel. Similarly, scent diffuser 100 may comprise only one adjustment panel. In the latter embodiment, the body portion 110 may comprise ventilation apertures extending through only one face surface, and the opposite face surface may be uninterrupted by ventilation apertures. In either of such embodiments, the rate of scent diffusion into the environment surrounding the scent diffuser may be at least substantially less than the embodiments discussed herein.

That which is claimed:

1. A scent diffuser comprising:
a hollow body defining a first open end and an opposite second open end;
a first scent panel slidably secured to the hollow body and at least partially saturated with a fragrance composition; and
a second scent panel slidably secured to the hollow body and at least partially saturated with the fragrance composition;
wherein the second scent panel is slidable relative to the first scent panel to adjust a rate of fragrance composition diffusion from each of the first scent panel and the second scent panel; and
wherein each of the first scent panel and the second scent panel are slidable between:
a compressed position in which a maximum surface area of the first scent panel and a maximum surface area of the second scent panel are each positioned within the hollow body; and
an expanded position in which a minimum surface area of the first scent panel and a minimum surface area of the second scent panel are each positioned within the hollow body and wherein the first scent panel extends through the first open end of the hollow body and the second scent panel extends through the second open end of the hollow body.

2. The scent diffuser of claim 1, wherein the hollow body has one or more sidewalls collectively defining a body interior.

3. The scent diffuser of claim 2, wherein the hollow body defines a first slide pin and a second slide pin, each of the first and second slide pins extending away from an interior surface of at least one sidewall into the body interior, and
wherein the first scent panel defines a groove slidably engaged with the first slide pin and the second scent panel defines a groove slidably engaged with the second slide pin; and
wherein
in the compressed position, the first and second slide pins are adjacent a first end of the grooves in the first scent panel and the second scent panel; and
in the expanded position, the first and second slide pins are adjacent a second end of the grooves in the first scent panel and the second scent panel.

4. The scent diffuser of claim 2, wherein each of the first scent panel and the second scent panel define at least two planar and parallel edge surfaces extending along opposite edges of each of the first scent panel and the second scent panel, and the at least two planar and parallel edge surfaces are frictionally engaged with planar and parallel surfaces of the body interior to maintain a desired position of the first scent panel and the second scent panel between the compressed position and the expanded position.

5. The scent diffuser of claim 1, further comprising a handle secured relative to an end of at least one of the first scent panel or the second scent panel.

6. The scent diffuser of claim 5, further comprising a lanyard secured relative to the handle.

7. The scent diffuser of claim 2, wherein an end of each of the first scent panel and the second scent panel is positioned outside of the hollow body when the first scent panel and the second scent panel is positioned in either the compressed position or the expanded position.

8. The scent diffuser of claim 2, wherein the first planar scent panel is slidable independently of the second planar scent panel.

9. The scent diffuser of claim 2, wherein the body comprises a rigid plastic material and each of the first scent panel and the second scent panel comprises a paper material.

10. The scent diffuser of claim 2, wherein:
the fragrance composition is configured to evaporate into air surrounding the scent diffuser at a first rate when the first scent panel and the second scent panel are in the compressed position; and
the fragrance composition is configured to evaporate into air surrounding the scent diffuser at a second rate when the first scent panel and the second scent panel are in the expanded position, wherein the second rate is greater than the first rate.

\* \* \* \* \*